United States Patent
Satou et al.

(10) Patent No.: US 11,761,902 B2
(45) Date of Patent: Sep. 19, 2023

(54) FOREIGN SUBSTANCE CHECKING SYSTEM

(71) Applicant: NIPRO CORPORATION, Osaka (JP)

(72) Inventors: Takuma Satou, Osaka (JP); Masamichi Takasugi, Osaka (JP)

(73) Assignee: NIPRO CORPORATION

(*) Notice: Subject to any disclaimer, the term of this patent is extended or adjusted under 35 U.S.C. 154(b) by 219 days.

(21) Appl. No.: 17/298,989

(22) PCT Filed: Oct. 29, 2019

(86) PCT No.: PCT/JP2019/042321
§ 371 (c)(1),
(2) Date: Jun. 2, 2021

(87) PCT Pub. No.: WO2020/116053
PCT Pub. Date: Jun. 11, 2020

(65) Prior Publication Data
US 2022/0050059 A1    Feb. 17, 2022

(30) Foreign Application Priority Data

Dec. 5, 2018  (JP) ................................. 2018-228259

(51) Int. Cl.
*G01N 21/00*  (2006.01)
*G06T 7/00*  (2017.01)
(Continued)

(52) U.S. Cl.
CPC ....... *G01N 21/9009* (2013.01); *G06T 7/0004* (2013.01); *G01N 2033/0081* (2013.01)

(58) Field of Classification Search
CPC .............. G01N 21/94; G01N 21/9027; G01N 21/9009; G01N 21/9036; G01N 2033/0081; G06T 7/0004
See application file for complete search history.

(56) References Cited

U.S. PATENT DOCUMENTS

2003/0041678 A1    3/2003  Hoshida et al.
2009/0294469 A1*  12/2009  Poulain ................. G01G 13/00
                                                          222/64
2014/0250835 A1    9/2014  Prabhu et al.

FOREIGN PATENT DOCUMENTS

EP          3875946 A1    9/2021
JP          01-155238 A   6/1989
(Continued)

OTHER PUBLICATIONS

Hideo et al "Foreign Matter Inspecting Device for Powder in Transparent Container", Oct. 24, 2000, JP 2000298103A (Year: 2000).*

(Continued)

*Primary Examiner* — Sang H Nguyen
(74) *Attorney, Agent, or Firm* — Jordan and Koda, PLLC

(57) ABSTRACT

To provide a means that is less likely to misidentify a crack as a foreign substance during an image checking in which a vibration is applied to a powder contained in a bag-like container. A foreign substance checking system includes a vibration device configured to apply a vibration to a container, a photography device configured to optically photograph the inside of the container through a transparent region from the outside, and a determination device configured to determine whether a foreign substance is present inside the container based on an image of the container photographed by the photography device. The vibration device includes a rotating shaft and a hammer rotating in conjunction with the rotating shaft and colliding with the container. A portion of an outer surface of the hammer to abut on the container has a flat surface.

14 Claims, 3 Drawing Sheets

(51) Int. Cl.
*G01N 21/90* (2006.01)
*G01N 33/00* (2006.01)

(56) References Cited

FOREIGN PATENT DOCUMENTS

| JP | 02-150752 A | 6/1990 |
| JP | 03-051748 A | 3/1991 |
| JP | 2000-298103 A | 10/2000 |
| JP | 2001-004549 A | 1/2001 |
| JP | 2003-166939 A | 6/2003 |
| JP | 2010-008339 A | 1/2010 |
| JP | 2014-006186 A | 1/2014 |

OTHER PUBLICATIONS

Kazuhisa "Image Forming Device", Jul. 3, 2003, JP 2003186288A (Year: 2000).*
Rudolf "Device For Inspecting Foreign Bodies In Filled Container Comprises Vibration Unit For Vibrating Container", May 4, 2006, DE 102004051961A (Year: 2006).*
Dudoft "Checkup for Foreign Matter in Filled Container", Aug. 25, 2014, JP 2014153355A (Year: 2014).*

* cited by examiner

FOREIGN SUBSTANCE CHECKING SYSTEM

BACKGROUND OF THE INVENTION

The present invention relates to a foreign substance checking system that checks whether a foreign substance is present inside a bag-like container in which a powder is sealed and which has a region where the powder is visible from the outside.

Conventionally, as a form in which powdered pharmaceuticals, such as powdered medicines, fine granules, granules, and injections are packaged, a bag-like container having a region where a powder is visible from the outside is mentioned. As a checking for the presence of a foreign substance in the powder contained in the container, a visual checking and a checking performed by analyzing optically obtained image data are known (Patent Document 1). A foreign substance detecting device described in Patent Document 1 optically detects a foreign substance in a powder when a vibration is applied to a bag-like body containing the powder.

Patent Document 1: Japanese Patent Application Laid-Open No. 2001-4549

SUMMARY OF THE INVENTION

However, when the vibration is applied to the bag-like body, a crack is sometimes generated in a powder mass. Since this crack appears as a shadow in an image, the shadow is sometimes determined as the foreign substance when the image is analyzed. As a result, a product, which is actually a good product in which no foreign substance is present, may be determined to be a defective product in which the foreign substance is present.

The present invention has been made in view of the above-described circumstances. An object of the present invention is to provide a means that is less likely to misidentify a crack as a foreign substance during an image checking in which a vibration is applied to a powder contained in a bag-like container.

(1) The present invention relates to a foreign substance checking system that checks whether a foreign substance is present inside a bag-like container in which a powder is sealed and which has a region where the powder is visible from an outside. The foreign substance checking system includes a vibration device configured to apply a vibration to the container, a photography device configured to optically photograph an inside of the container through the region from the outside, and a determination device configured to determine whether the foreign substance is present inside the container based on an image of the container photographed by the photography device. The vibration device includes a rotating shaft and a hammer rotating in conjunction with the rotating shaft and colliding with the container. A region of an outer surface of the hammer to collide with the container has a flat surface.

By making the hammer collide with the container to apply a vibration to the container, the foreign substance buried inside the powder can be made to appear so that the foreign substance can be photographed. By making the hammer collide with the container to apply a vibration to the container, the foreign substance buried inside the powder can be made to appear so that the foreign substance can be photographed. Since the region of the outer surface of the hammer to collide with the container has the flat surface, a crack is less likely to be generated in the powder and the foreign substance that appears is less likely to disappear. With this, based on the obtained image, an accuracy of determining whether the foreign substance other than the powder is present inside the container is improved.

(2) Preferably, a ratio of a collision area of an outer surface, on the hammer, which collides with the outer surface of the container to a work area corresponding to a space in which the powder can be sealed, on an outer surface of the container on which the hammer abuts is within a range of 1 to 4%.

Since the collision area with respect to the work area is within the range of 1 to 4%, the crack is less likely to be generated in the powder and the foreign substance that appears is less likely to disappear. With this, based on the obtained image, the accuracy of determining whether the foreign substance other than the powder is present inside the container is improved.

(3) Preferably, the vibration device includes a plurality of the hammers in conjunction with one rotating shaft, and the collision area is a sum of an area of an outer surface, on each of the hammers, the region colliding with the outer surface of the container.

(4) Preferably, the vibration device includes a plurality of sets of the plurality of the hammers in conjunction with one rotating shaft.

(5) Preferably, an area of an outer surface of one hammer to collide with the outer surface of the container is within a range of 15 to 25 square millimeters.

(6) Preferably, the work area is within a range of 4000 to 7000 square millimeters.

(7) Preferably, a weight of the powder sealed in the container is within a range of 0.20 to 10 grams.

(8) Preferably, the hammer comprises an elastic body.

(9) Preferably, an outer surface of the container with which the outer surface of the hammer collides has a flat surface.

According to the present invention, it is less likely to misidentify a crack as the foreign substance during an image checking in which the vibration is applied to the powder contained in the bag-like container.

DESCRIPTION OF EMBODIMENTS

Hereinafter, an embodiment of the present invention will be described with reference to the drawings as appropriate. It is a matter of course that the embodiment described below is merely an example of the present invention, and the embodiment of the present invention can be appropriately modified without changing the gist of the present invention. In the following description, a vertical direction 5 is defined based on the top and the bottom, a forward and backward direction 6 (direction perpendicular to the sheet surface of FIG. 2) is defined in a direction perpendicular to the vertical direction 5, and a left and right direction 7 is defined in a direction perpendicular to each of the vertical direction 5 and the forward and backward direction 6.

Figure 1:
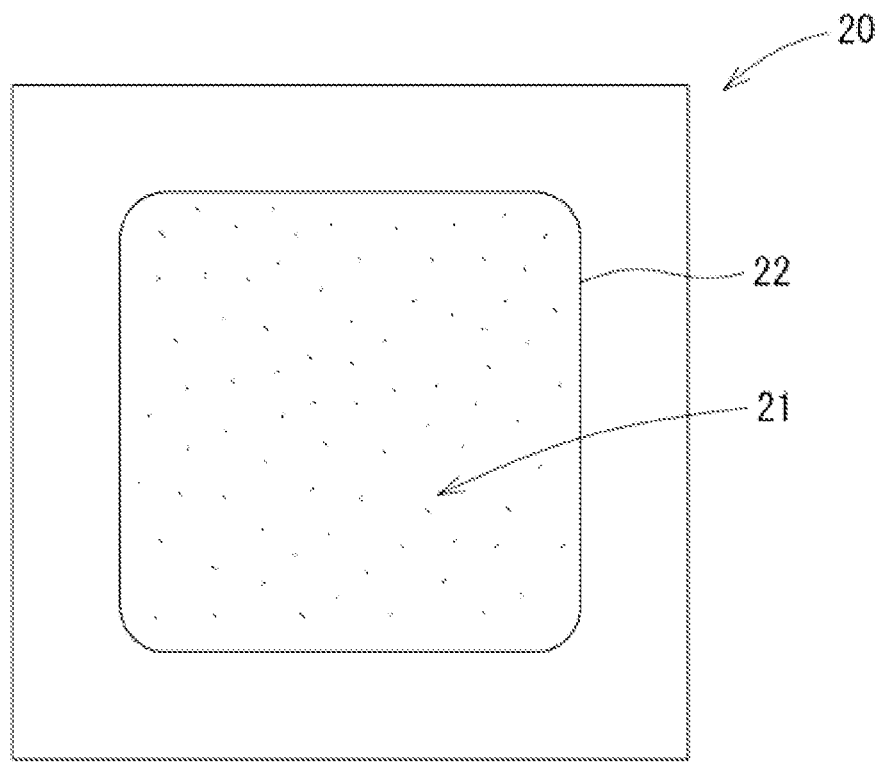
FIG. 1 is a plan view of a container 20.

As illustrated in FIG. 1, an object to be checked by a foreign substance checking system 10 described later is a container 20 in which a powder 21 is contained. The powder 21 is a pharmaceutical agent, such as powdered medicines, fine granules, granules, and injections. The pharmaceutical agents are not particularly limited, and, for example, cell wall synthesis inhibitor antibiotics, cell membrane inhibitor antibiotics, nucleic acid synthesis inhibitor antibiotics, protein synthesis inhibitor antibiotics, folic acid metabolic pathway inhibitor antibiotics, β-lactamase inhibitors, sulfa drugs, and anti-infective drugs are preferable. Examples of the pharmaceutical agents include ampicillin, bacampicillin, amoxicillin, pivmecillinam, amoxicillin, sultamicillin, piperacillin, aspoxicillin, benzylpenicillin, cloxacillin, oxacillin, carbenicillin, cefaclor, cefroxadine, cefadroxil, cefixime, cefteram pivoxil, cefuroxime axetil, cefpodoxime proxetil, cefotiam hexetil, cefdinir, ceftibuten, cefditoren pivoxil, cefcapene pivoxil, cefazolin, cefozopran, cefmetazole, cefotiam, cefsulodin, cefoperazone, cefotaxime, cefmenoxime, ceftriaxone, ceftazidime, cefodizime, cefpirome, cefepime, faropenem, imipenem, panipenem, meropenem, biapenem, doripenem, aztreonam, vancomycin, teicoplanin, fosmicin, polymixin B sulfate, colistin sulfate, gramicidin S, amphotericin B, levofloxacin, ofloxacin, norfloxacin, enoxacin, ciprofloxacin, lomefloxacin, tosufloxacin, sparfloxacin, gatifloxacin, prulifloxacin, moxifloxacin, pazufloxacin, rifampicin, dibekacin, tobramycin, amikacin, isepamicin, micronomicin, streptomycin, kanamycin, gentamicin, erythromycin, rokitamycin, josamycin, roxithromycin, clarithromycin, azithromycin, telithromycin, doxycycline, minocycline, chloramphenicol, lincomycin, clindamycin, trimethoprim, clavulanic acid, sulbactam, tazobactam, sulfamethoxazole, salazopyrin, isoniazid, rifampicin, pyrazinamide, ethambutol, griseofulvin, amphotericin B, 5-fluorocytosine, fluconazole, miconazole, itraconazole, aciclovir, ganciclovir, foscavir, idoxuridine, amantadine, interferon γ, ribavirin, lamivudine, metronidazole, tinidazole, fluconazole, mebendazole, pyrantel pamoate, diethylcarbamazine, praziquantel, albendazole, ivermectin, quinupristin, dalfopristin, linezolid, spectinomycin, netilmicin, sisomycin, lincosamin, ramoplanin, telithromycin, nystatin, fusidic acid, chlorhexidine, polyhexanide, and the like.

As the properties of the powder 21 that is easily cracked by the application of a vibration, the angle of repose, the particle size, and the filling amount can be mentioned, for example. The angle of repose of the powder 21 is relatively low and specifically less than 46° and preferably less than 45°. The particle size of the powder 21 is large, and specifically the average particle size is 60 μm or more and preferably 64 μm or more.

The filling amount of the powder 21 contained in the container 20 is preferably within a range of 0.2 g to 10 g, and more preferably within a range of 0.2 g to 5 g. When the filling amount of the powder 21 contained in the container 20 is less than each of the above ranges, a crack is less likely to be generated in the powder 21. Meanwhile, when the filling amount of the powder 21 contained in the container 20 is larger than each of the above ranges, a foreign substance mixed in the powder 21 is less likely to appear.

The container 20 has a rectangular bag shape in a plan view, capable of containing the powder 21 therein. The container 20 is formed by thermally fusion-bonding laminate sheets obtained by laminating a plurality of synthetic resin sheets, for example. In one surface of the bag-like container 20, a transparent region 22 is formed. The transparent region 22 is formed of a transparent resin sheet. The powder 21 contained in the internal space is visible through the transparent region 22.

In the present embodiment, the transparent region 22 is formed on an outer surface of the container 20 over an entire space in which the powder 21 can be contained. Therefore, the transparent region 22 is a work area with which a hammer 32 can collide. The work area is preferably within a range of 4000 mm$^2$ to 7000 mm$^2$, and more preferably within a range of 4800 mm$^2$ to 6000 mm$^2$. When the work area is smaller than the above ranges, a crack is likely to be generated, because an impact caused by the collision of the hammer 32 becomes local. Meanwhile, when the work area is larger than the above ranges, the impact caused by the collision of the hammer 32 is dispersed, and the foreign substance mixed in the powder 21 is less likely to appear.

Figure 2:
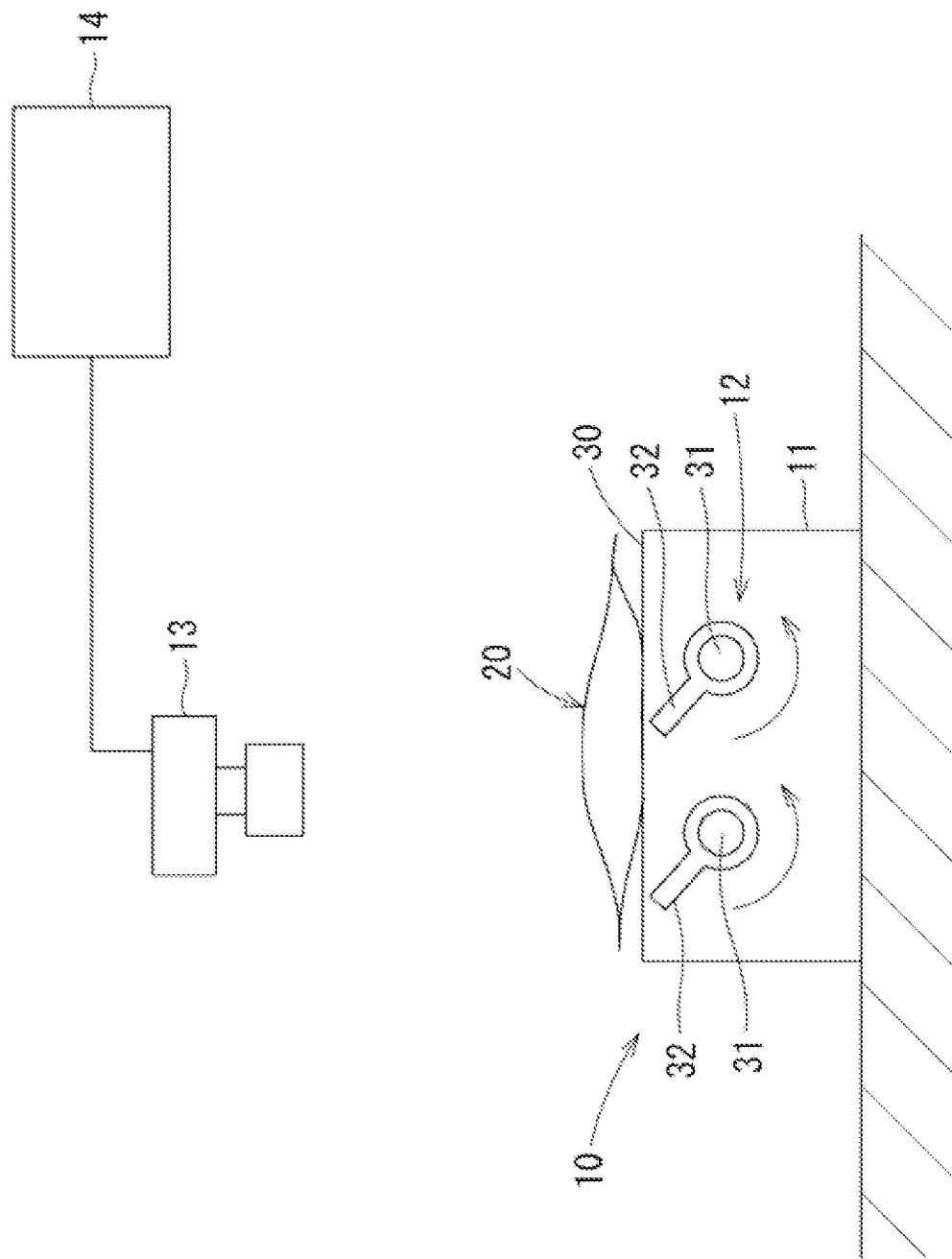
FIG. 2 is a schematic view of a foreign substance checking system 10.

As illustrated in FIG. 2, the foreign substance checking system 10 includes a support base 11, a vibration device 12, a photography device 13, and a determination device 14.

The support base 11 is a flat base on which the container 20 can be mounted on its upper surface. Hammers 32 of the vibration device 12 are located in a cavity at the center of the upper surface 30 of the support base 11. The upper surface 30 of the support base 11 supports a peripheral portion of the container 20. The container 20 is supported by the support base 11 so that the transparent region 22 faces upward. An outer surface of the container 20 exposed downward from the cavity of the upper surface 30 of the support base 11 forms a flat surface which is substantially along a horizontal direction. An area of the outer surface of the container 20 exposed downward from the cavity of the upper surface 30 of the support base 11 is the work area. Although not illustrated, the support base 11 may be provided with a clip for fixing the container 20 or a suction port for sucking and fixing the container 20. Further, to make the support base 11 support the containers 20 sequentially, a transport device may be provided.

Below the upper surface 30 of the support base 11, the vibration device 12 is located. The vibration device 12 has rotating shafts 31 and the hammers 32 rotating in conjunction with the rotating shafts 31 and colliding with the container 20. In this embodiment, two rotating shafts 31 are located apart from each other in the left and right direction along the forward and backward direction 6 (direction perpendicular to the sheet surface of FIG. 2). Each of the two rotating shafts 31 rotates by the transmission of rotation from a motor (not illustrated).

Two or more of the hammers 32 are fixed apart from each other in the forward and backward direction 6 with respect to one rotating shaft 31. The hammers 32 are formed of an elastic material, such as chlorinated butyl rubber, butyl rubber, and silicone rubber. Although in this embodiment, the plurality of hammers 32 fixed to one rotating shaft 31 project in the same direction from the rotating shaft 31, the directions in which the plurality of hammers 32 project from the rotating shaft 31 may be different.

Figure 3:
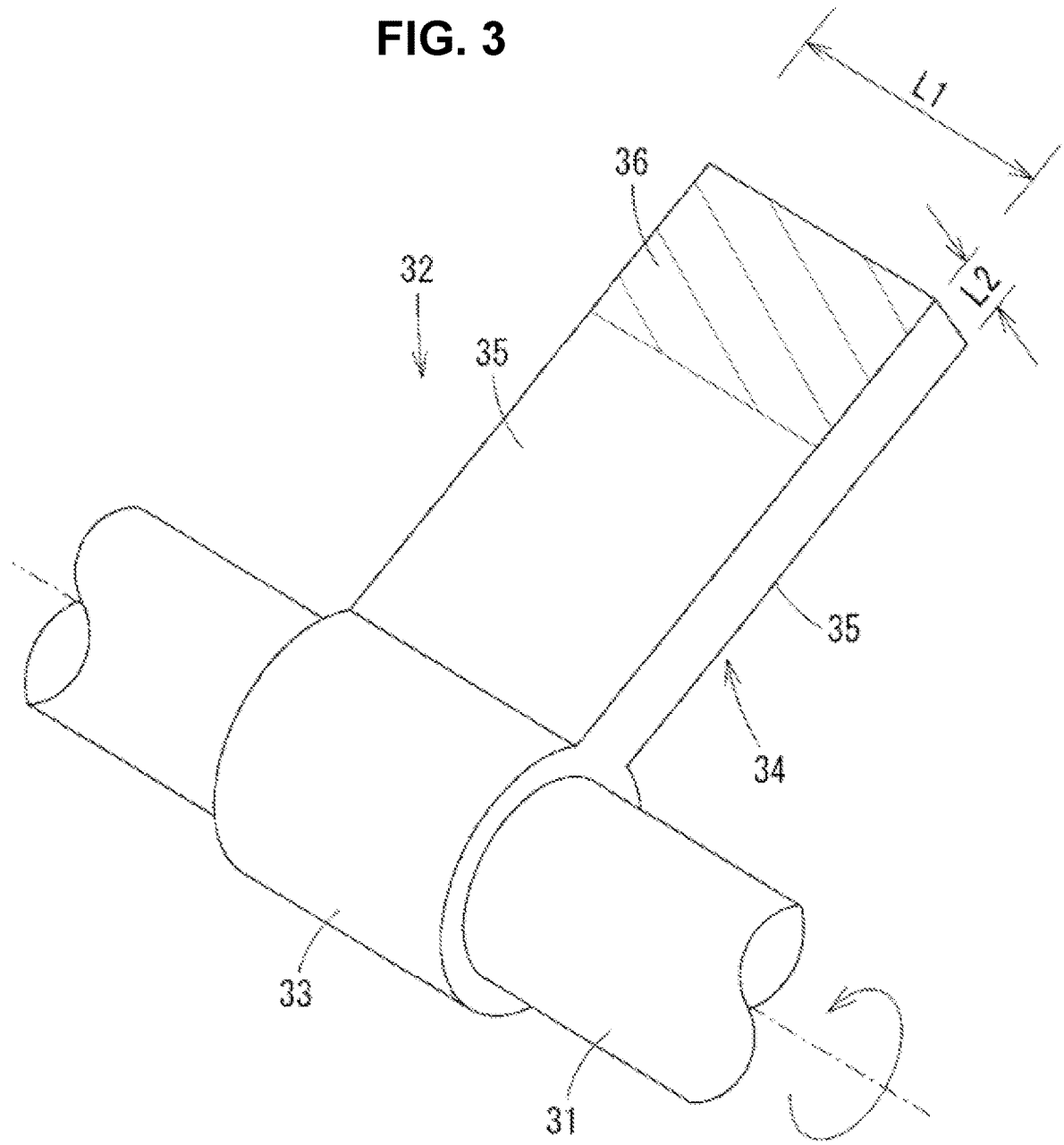
FIG. 3 is an external perspective view of a hammer 32.

Since a shape of each hammer 32 is the same, a shape of one hammer 32 will be described. As illustrated in FIG. 3, the hammer 32 has an annular portion 33 that is externally fitted to the rotating shaft 31, and a convex portion 34 that projects from the annular portion 33 in a radial direction of the rotating shaft 31. The annular portion 33 has a cylindrical shape. The rotating shaft 31 is inserted into a hollow of the annular portion 33, and the annular portion 33 rotates integrally with the rotating shaft 31.

The convex portion 34 has a quadrangular prism shape. Among outer surfaces of the convex portion 34, outer surfaces 35 along the rotating shaft 31 have a flat surface. One of the two outer surfaces 35 is a surface that can collide with the outer surface of the container 20. Which outer surface 35 of the two outer surfaces 35 collides with the outer surface of the container 20 depends on a rotation direction of the rotating shaft 31. Further, a portion of the outer surface 35 of the convex portion 34 collides with the outer surface of the container 20. The portion of the outer surface 35 that can collide with the outer surface of the container 20 depends on a distance between the rotating shaft 31 and the outer surface of the container 20 and a projecting length of the convex portion 34. It is preferable that a portion of the outer surface 35 including a tip in a projecting direction collide with the outer surface of the container 20. That is, the outer surface 35 of the hammer 32 and the outer surface of the container 20 are in a surface contact in which flat surfaces are in contact with each other. In FIG. 3, the portion of the outer surface 35 that can collide with the outer surface of the container 20 is hatched and is indicated by a reference numeral 36. An area of the portion 36 (an example of a region) is a collision area. In the present embodiment, since a plurality of hammers 32 are provided, the collision area is a total value of an area of the portion 36 of the outer surface 35 of each hammer 32. The collision area can be adjusted by the distance between the rotating shaft 31 and the container 20, the projecting length of the convex portion 34, and a projecting width of the convex portion 34. Since the portion 36 of the outer surface 35 of the hammer 32 has a flat surface, the crack is less likely to be generated in the powder 21, and the foreign substance that appears from the powder 21 is less likely to disappear.

The area of the portion 36 of the outer surface 35 with respect to the work area, that is, a ratio of the collision area is preferably 0.8% or more, more preferably within a range of 1% to 4%, particularly preferably within a range of 1.1% to 3.7%, and further preferably within a range of 1.7% to 3.05%. When the ratio of the collision area to the work area is smaller than the above ranges, an area where the impact of the hammer 32 colliding with the container 20 is transmitted becomes small, and the crack is less likely to be generated in the powder 21. When the ratio of the collision area to the work area is larger than the above ranges, the impact caused by the collision of the hammer 32 is dispersed, and the foreign substance mixed in the powder 21 is less likely to appear.

In the convex portion 34, a length L1 along an axial direction of the rotating shaft 31 is longer than a length L2 along a tangential direction with respect to a circumferential direction of the rotating shaft 31 (L1>L2). In a state where the hammer 32 projects substantially upward from the rotating shaft 31, the hammer 32 can abut on the container 20 supported by the upper surface 30 of the support base 11. The rotation of rotating shaft 31 alternately generates timings when the hammers 32 abut on the container 20 and timings when the hammers 32 are separated from the container 20, and as a result, the hammers 32 strike the container 20. By the striking of the hammers 32 described above, a vibration is applied to the container 20.

By making the hammers 32 collide with the container 20 to apply a vibration to the container 20, the foreign substance buried inside the powder 21 can be made to appear so that the foreign substance can be photographed. Since the collision area with respect to the work area is within the range of 1 to 4%, the crack is less likely to be generated in the powder 21 and the foreign substance that appears is less likely to disappear. With this, based on the obtained image, an accuracy of determining whether the foreign substance other than the powder 21 is present inside the container 20 is improved.

The photography device 13 is located above the upper surface 30 of the support base 11. In other words, the photography device 13 is located on the opposite side to the vibration device 12 in the vertical direction 5, with the container 20 supported by the upper surface 30 of the support base 11 interposed between the vibration device 12 and the photography device 13. The photography device 13 optically photographs the inside of the container 20 through the transparent region 22 from the outside of the container 20, and is a monochrome CCD camera, for example. The photography device outputs the photographed image as image data. The photography device 13 photographs 30 images per second, for example, and outputs the images as the image data.

The determination device 14 can receive the image data output from the photography device 13. The determination device 14 determines whether a foreign substance is present inside the container 20 based on the images of the container 20 photographed by the photography device 13, i.e., the image data. Specifically, the obtained one piece of image data is vertically and horizontally divided into a predetermined number of regions, and the color density of each region is identified in a plurality of stages. When the powder 21 is white, the foreign substance is recognized as black. Then, it is determined whether the foreign substance is present from a peak value (color density of foreign substance), an intensity volume value (height×width×color density of foreign substance), and an intensity area value (height×width of foreign substance) in the image data. For example, when all of the peak value, the intensity volume value, and the intensity area value are within predetermined conditions, e.g., when there is a predetermined continuous range where each value is equal to or higher than a threshold value, the determination device 14 determines that the foreign substance is present in the container 20.

EXAMPLE

Hereinafter, an example of a foreign substance checking method using the foreign substance checking system 10 will be described.

Example 1: The number of the hammers 32 was seven, and an outer surface of a collision portion of each hammer 32 had a flat surface. The collision area of each hammer 32 was within a range of 15 mm$^2$ to 25 mm$^2$. A total collision area of the seven hammers 32 was within a range of 105 mm$^2$ to 175 mm$^2$. Further, the work area of the container 20 was set to 6000 mm$^2$. Therefore, a ratio of the collision area of the hammers 32 to the work area was about 1.75% to 2.92%.

Comparative Example 1: The number of the hammers 32 was seven, and the collision portion of each hammer 32 was a convex portion which was a corner of a triangular prism. The collision area of each hammer 32 was 5 mm$^2$. The total collision area of the seven hammers 32 was 35 mm$^2$. Further, the work area of the container 20 was set to 6000 mm$^2$. Therefore, the ratio of the collision area of the hammers 32 to the work area was about 0.58%.

Good product misdetection rate: A test was performed on 88 bags of the container 20 using the foreign substance checking system 10 according to Example 1, and a percentage was obtained by counting the number of containers 20 with respect to which the foreign substance was determined to be mixed. Further, a test was performed on 10 bags of the container using the foreign substance checking system 10 according to Comparative Example 1, and a percentage was obtained by counting the number of containers with respect to which the foreign substance was determined to be mixed. The results are shown in Table 1.

Foreign substance detection rate: One of a carbon powder having an outer diameter of about 300 μm, a stainless powder having an outer diameter of about 1000 μm, and a black polypropylene powder having an outer diameter of about 3000 μm was mixed in each container 20, a test was performed on 20 bags of the container 20 using the foreign substance checking system 10 according to Example 1, and a percentage was obtained by counting the number of containers 20 with respect to which the foreign substance was determined to be mixed. The results are shown in Table 1.

TABLE 1

Good product misdetection rate and foreign substance detection rate

|  | Good product misdetection rate | Carbon powder | Stainless powder | Polypropylene powder |
|---|---|---|---|---|
| Example 1 | 0% | 100% | 100% | 100% |
| Comparative Example 1 | 30% | — | — | — |

As illustrated in Table 1, the good product misdetection rate was 0% in Example 1. In contrast, the good product misdetection rate was 30% in Comparative Example 1. Further, in Example 1, a foreign substance contamination was detected in all of the containers 20 in which the carbon powder, the stainless powder, or the polypropylene powder was mixed.

DESCRIPTION OF REFERENCE NUMERALS 10 foreign substance checking system
12 vibration device
13 photography device
14 determination device
20 container
21 powder
22 transparent region (work area)
31 rotating shaft
32 hammer
35 outer surface
36 portion (collision area)

The invention claimed is:

1. A foreign substance checking system that checks whether a foreign substance is present inside a bag-like container in which a powder is sealed and which has a region where the powder is visible from an outside,
the foreign substance checking system comprising:
a vibration device configured to apply a vibration to the container;
a photography device configured to optically photograph an inside of the container through the region from the outside; and
a determination device configured to determine whether the foreign substance is present inside the container based on an image of the container photographed by the photography device, wherein
the vibration device includes a rotating shaft and a hammer rotating in conjunction with the rotating shaft and colliding with the container, and
wherein the hammer includes a first surface extending radially relative to the rotating shaft, the first surface having a flat surface region configured to collide with the container.

2. The foreign substance checking system according to claim 1, wherein a weight of the powder sealed in the container is within a range of 0.20 to 10 grams.

3. The foreign substance checking system according to claim 1, wherein the hammer comprises an elastic body.

4. The foreign substance checking system according to claim 1, wherein an outer surface of the container with which the region of the outer surface of the hammer collides has a flat surface.

5. The foreign substance checking system according to claim 1, wherein the vibration device is configured to have the rotating shaft rotate in a first direction and bring the flat surface region of the first surface repeatedly into and out of contact with the container as the rotating shaft continues rotating in the first direction.

6. The foreign substance checking system according to claim 5, wherein the hammer is comprised of an elastic material adapted to allow flat surface contact between a flat surface of the container and the first surface of the hammer, wherein the flat surface region of the first surface is configured to extend radially relative to the rotating shaft at least while the hammer is out of contact with the container.

7. The foreign substance checking system according to claim 5, wherein a ratio of the flat surface region to a work area corresponding to a space in which the powder can be sealed, on an outer surface of the container on which the hammer abuts is within a range of 1 to 4%.

8. The foreign substance checking system according to claim 5, wherein the vibration device includes a plurality of the hammers in conjunction with one rotating shaft, wherein a collision area is a sum of an area of the flat surface region of each one hammer, colliding with a corresponding outer surface area of the container.

9. The foreign substance checking system according to claim 8, wherein the flat surface region of each one hammer is within a range of 15 to 25 square millimeters.

10. A foreign substance checking system that checks whether a foreign substance is present inside a bag-like container in which a powder is sealed and which has a region where the powder is visible from an outside,
the foreign substance checking system comprising:
a vibration device configured to apply a vibration to the container;
a photography device configured to optically photograph an inside of the container through the region from the outside; and
a determination device configured to determine whether the foreign substance is present inside the container based on an image of the container photographed by the photography device, wherein
the vibration device includes a rotating shaft and a hammer rotating in conjunction with the rotating shaft and colliding with the container, and
a region of an outer surface of the hammer to collide with the container has a flat surface; and
wherein a ratio of a collision area, which is an area of the region on the outer surface of the hammer, to a work area corresponding to a space in which the powder can be sealed, on an outer surface of the container on which the hammer abuts is within a range of 1 to 4%.

11. The foreign substance checking system according to claim 10, wherein the vibration device includes a plurality of the hammers in conjunction with one rotating shaft, and the collision area is a sum of an area of a region of an outer surface, on each of the hammers, the region colliding with the outer surface of the container.

12. The foreign substance checking system according to claim 11, wherein the vibration device includes a plurality of sets of the plurality of the hammers in conjunction with one rotating shaft.

13. The foreign substance checking system according to claim 10, wherein an area of an outer surface of one hammer to collide with the outer surface of the container is within a range of 15 to 25 square millimeters.

14. The foreign substance checking system according to claim 10, wherein the work area is within a range of 4000 to 7000 square millimeters.

\* \* \* \* \*